United States Patent
Nguyen

(10) Patent No.: US 12,133,876 B2
(45) Date of Patent: Nov. 5, 2024

(54) TRYNOVID BOOSTS IMMUNE SYSTEM AGAINST VIRUSES AND VARIANTS

(71) Applicant: Peter Nguyen, Garden Grove, CA (US)

(72) Inventor: Peter Nguyen, Garden Grove, CA (US)

(73) Assignee: Peter Nguyen, Garden Grove, CA (US)

( * ) Notice: Subject to any disclaimer, the term of this patent is extended or adjusted under 35 U.S.C. 154(b) by 0 days.

(21) Appl. No.: 17/567,892

(22) Filed: Jan. 4, 2022

(65) Prior Publication Data
US 2024/0216461 A1  Jul. 4, 2024

(51) Int. Cl.

| | | |
|---|---|---|
| *A61K 36/63* | (2006.01) | |
| *A61K 9/00* | (2006.01) | |
| *A61K 31/122* | (2006.01) | |
| *A61K 31/22* | (2006.01) | |
| *A61K 31/593* | (2006.01) | |
| *A61K 35/644* | (2015.01) | |
| *A61K 36/28* | (2006.01) | |
| *A61K 36/48* | (2006.01) | |
| *A61K 36/53* | (2006.01) | |
| *A61K 36/61* | (2006.01) | |
| *A61K 36/889* | (2006.01) | |

(52) U.S. Cl.
CPC ............ *A61K 36/63* (2013.01); *A61K 9/0053* (2013.01); *A61K 31/122* (2013.01); *A61K 31/22* (2013.01); *A61K 31/593* (2013.01); *A61K 35/644* (2013.01); *A61K 36/28* (2013.01); *A61K 36/48* (2013.01); *A61K 36/53* (2013.01); *A61K 36/61* (2013.01); *A61K 36/889* (2013.01)

(58) Field of Classification Search
CPC ........ A61K 36/63; A61K 36/61; A61K 36/53; A61K 31/593; A61K 31/122
See application file for complete search history.

(56) References Cited

U.S. PATENT DOCUMENTS

| | | | | |
|---|---|---|---|---|
| 8,168,611 B1 * | 5/2012 | Perrin | ..................... | A23L 33/12 |
| | | | | 514/276 |
| 8,197,866 B1 * | 6/2012 | Lukacs | .................. | A61K 36/63 |
| | | | | 424/732 |

FOREIGN PATENT DOCUMENTS

| | | | | |
|---|---|---|---|---|
| JP | 2011046651 A | * | 3/2011 | |
| JP | 2013060405 A | * | 4/2013 | |

* cited by examiner

*Primary Examiner* — Kyle A Purdy

(57) ABSTRACT

In summary, the present disclosure is directed to a soft gel food supplement; formulated in eleven natural antiviral ingredients; to boost the immune system. The present disclosure contains natural antiviral antibacterial ingredients that makes the human immune system a more complex network of cells and proteins that defends the body against infection. The immune system keeps a record of every germ (microbe) it has ever defeated so it can recognize and destroy the microbe quickly if it enters the body again.
Covid will attack everybody in its path. However, when a variant attempts to infect those who use the present disclosure dietary supplement formula and method, the immune system is nourished and ready to boost its normal function to the utmost in recognizing and destroying the virus and its variants efficiently.

2 Claims, 1 Drawing Sheet

CUSTOM LABELED BOTTLE OF SOFT GEL FOOD SUPPLEMENT
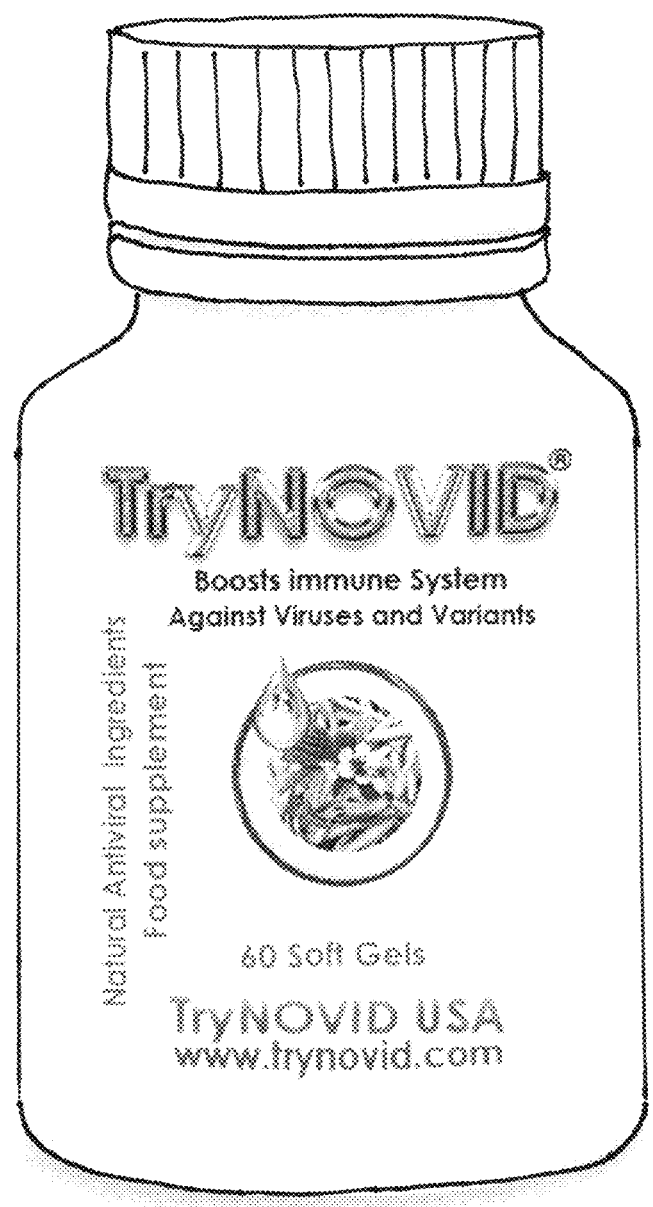

TRYNOVID BOOSTS IMMUNE SYSTEM AGAINST VIRUSES AND VARIANTS

FIELD OF THE PRESENT DISCLOSURE

The present disclosure is directed to a soft gel dietary supplement; formulated in eleven natural antiviral ingredients; to boost the immune system against viruses and variants. The present disclosure contains natural antiviral antibacterial ingredients that makes the human immune system a more complex network of cells and proteins that defends the body against infection. Covid will attack everybody in its path. However, when a variant attempts to infect those who use the present disclosure soft gel food supplement, the immune system is ready to boost its normal function to the utmost in recognizing and destroying the virus and its variants efficiently.

The information presented below is a compilation of scientific evidence and research that supports not only the health benefits of said soft gel food supplement, but also the therapy theory of antiviral antibiotics that recognize and destroy viruses and variants every time they attempt to enter the human body.

BACKGROUND OF THE PRESENT DISCLOSURE

In early 2020, after a December 2019 outbreak in China, the World Health Organization identified SARS-COV-2 as a new type of Coronavirus. The outbreak quickly spread around the world. The disease caused by SARS-COV-2 can trigger a respiratory tract infection. It can affect upper respiratory tract (sinuses, nose, and throat) or lower respiratory tract (windpipe and lungs). It spreads the same way other viruses do, mainly through person-to-person contact. Infections range from mild to deadly. It is also normal for a virus to change, or mutate, as it infects people, Coronavirus has done so. There are several variants that are now spreading, some proving to be more contagious as well as more deadly than the original virus. Throughout the pandemic, scientists have kept a close eye on variants like: Alpha, Beta, Gamma, Delta, Omicron, Lambda, Mu . . . .

There is no way to tell how long the pandemic will continue. There are many factors, including the public's efforts to slow the spread, researchers' work to learn more about the virus, their search for a treatment, and the success of the vaccines. The Centers for Disease Control and Prevention (CDC) reports that as of Dec. 14, 2021, roughly 85% of adults ages 18 and over in the United States had received at least one dose of COVID-19 vaccine. However, 15% remained unvaccinated. Unvaccinated adults who responded to the survey reported that they were concerned about possible side effects of the vaccine (50%) or that they "don't trust the COVID-19 vaccine" (42%).

The present disclosure of said soft gel food supplement designed to create new strategies that reduce the impact of the pandemic cause by the SARS-COV-2 in our society. When a body collectively takes eleven natural ingredients contained in the said soft gel food supplement, the immune system is nourish and ready to boost its normal function to the utmost to recognize and destroy both viruses and their variants beforehand. In addition, the present disclosure soft gel food supplement enhances natural immune system's building blocks that do not allow virus to spread.

DETAIL DESCRIPTION OF THE PRESENT DISCLOSURE

The cellular membrane is composed of lipids. Therefore, doctors and patients are frustrated as some treatments can't get to the virus and its variants because the cell walls actually protect them! But essential oils such as thymol and monolaurin in the present disclosure are lipid soluble and small, they have no problem crossing the membrane. These antiviral ingredients do not depend on cellular transport mechanisms to enter the cell, they can easily cross the cell membrane and provide benefits directly to the cell. The ingredients in the present disclosure have been carefully chosen based on the scientific knowledge presented in this document, formulating as follows:

I. Formula of Eleven Chosen Natural Antiviral Ingredients:
   Monolaurin (90%)
   Vitamin D3 (100,000 IU/g in Safflower Oil)
   Vitamin K2 MK-4 (Menatetrenone-4)
   *Copaiba* Balsam Oil
   Red Thyme oil
   *Eucalyptus* oil (79% Eucalyptol)
   Bee propolis Powder Extract
   Virgin Coconut Oil (Organic)
   Sunflower Lecithin
   Yellow Beeswax
   Extra Virgin Olive Oil (Cold-Pressed)

Doses: We recommend 2 capsules a day. One to be taken in the morning and one to be taken at night. Not to be taken by anyone under the age 12 years.

Warning: Not to be taken if you are suffering from: Renal issues, Sarcoidosis, Coconut allergy. Consult a healthcare provider prior to use if pregnant, nursing, on medications, have a medical condition or are planning a medical procedure. Stop use and contact a physician if adverse reactions occur.

II. Therapeutic Theory:

1. MONOLAURIN

Monolaurin, also known as glycerol monolaurate (GML), it is the monoester formed from glycerol and lauric acid. Monolaurin is found in coconut oil and may be like other monoglycerides found in human breast milk. Lauric acid can be ingested in, and the human body converts it into monolaurin, furthermore, coconut oil, coconut cream, grated coconut and other products are excellent sources of lauric acid and, consequently, monolaurin (Brink, Chichlowski, Pastor, Narayanappa, & Shah, 2021). Research has shown that monolaurin exerts virucidal and bactericidal effects by solubilizing the lipids and phospholipids in the envelope of the pathogen causing the disintegration of its envelope. Recent evidence has also indicated that the antimicrobial effect is related to its interference with signal transduction in cell replication (Lieberman, Enig, & Preuss, 2006) Monolaurin has been shown to be able to inactivate enveloped viruses such as Coronavirus, Human Immunodeficiency virus (HIV), Measles virus, Herpes simplex virus type 1 and 2, Human lymphotropic viruses (type 1), Vesicular stomatitis virus, Visna virus, Cytomegalovirus, EpsteinBarr virus, Influenza virus, Pneumonovirus, Sarcoma virus, Syncytial virus, Rubeola virus (Lieberman et al., 2006).

2. VITAMIN D

Vitamin D3 significantly boosts the immune system which is the first target of the Coronavirus. In succinct positioning, Vitamin D3 enhances the immune system so that virus cannot attack the respiratory system that causes acute-severe respiratory distress. Vitamin D is a group of fat-soluble secosteroids responsible for increasing intestinal absorption of calcium, magnesium, and phosphate, and many other biological effects. In humans, the most important compounds in this group are vitamin D3 (also known as cholecalciferol) and vitamin D2 (ergocalciferol). Vitamin D has been recognized as essential to the skeletal system and plays a major role in monitoring the immune system, perhaps including immune reactions to viral infection. The severity of influenza and respiratory-tract infections may be increased by vitamin D deficiency. Cell-culture studies have shown that vitamin D has a particular role against enveloped viruses, such as the Coronavirus and direct antiviral effects. This might be because of the ability of vitamin D to upregulate human beta β-defensin2 and microbial peptide and it is known that coronavirus is an enveloped virus. During the COVID-19 pandemic, a high portion of moderate-severe cases and a high fatality rate have been observed among the elderly. Chronic municable diseases, obesity, and overweightness are related with vitamin D deficiency. A randomized pilot study that assessed the effect of calcifediol treatment and best-available therapy versus best-available therapy on intensive care unit (ICU) admission and mortality among patients hospitalized for COVID-19 demonstrated that administration of a high dose of calcifediol or 25-hydroxyvitamin D (25[OH]D), the main metabolite of vitamin D, significantly reduced the need for ICU treatment of patients requiring hospitalization due to proven COVID-19 (Yisak et al., 2021). Correlational and cross-sectional observational studies performed in various parts of the world have shown that vitamin D-deficient areas have a higher prevalence of COVID-19 patients (Pereira, Dantas Damascena, Galvão Azevedo, de Almeida Oliveira, & da Mota Santana, 2020; Yisak et al., 2021)

Most of the articles demonstrated that vitamin D status in the blood can determine the chances of catching corona virus, coronavirus severity, and mortality. Therefore, keeping appropriate blood levels of vitamin D through supplementation is recommended for the public to be able to cope with the pandemic (Yisak et al., 2021).

3. VITAMIN K

Vitamin K refers to structurally similar, fat-soluble vitamers found in foods and marketed as dietary supplements. The human body requires vitamin K for post-synthesis modification of certain proteins that are required for blood coagulation (K from koagulation, Danish for "coagulation") or for controlling binding of calcium in bones and other tissues. Some studies suggest that a vitamin K deficiency can aggravate the pneumonia caused by COVID-19, since our body is unable to stop the proteolysis of elastic fibers induced by COVID19, when there is a deficiency of this protein (Dofferhoff et al., 2020; Vlasschaert, Goss, Pilkey, Mckeown, & Holden, 2020). This research proposes a potential mechanism related to pneumonia that could induce the depletion proposes a potential mechanism related to pneumonia that could induce the depletion of vitamin K, which would cause an increase in lung damage and coagulopathy. The potential role of vitamin K supplements in preventing the development and progression of COVID-19 disease should be one of several strategies to consider in future research (Dofferhoff et al., 2020).

4. COPAIBA BALSAM OIL

*Copaiba* balsam oil collected from the trunk of trees that belong to the *Copaifera* species. *Copaiba* balsam is processed to make *Copaiba* oil. Both *Copaiba* balsam and *Copaiba* oil are used to make medicine. People take *Copaiba* balsam for treating bronchitis, hemorrhoids, constipation, diarrhea, and bladder infections and other urinary tract infections (UTIs). In pharmaceutical preparations, both *Copaiba* balsam and *Copaiba* oil are used in cough medicines and diuretics. Chemicals in *Copaiba* balsam and *Copaiba* oil might help kill germs. Other chemicals in *Copaiba* balsam might decrease swelling (inflammation), increase the production of urine (act as a diuretic), and help loosen chest congestion (act as an expectorant).

The oleoresin of *Copaifera* trees has been widely used as a traditional medicine in Neotropical regions for thousands of years and remains a popular treatment for a variety of ailments. The *Copaiba* resins are generally composed of a volatile oil made up largely of sesquiterpene hydrocarbons, such as -caryophyllene, -copaene, -elemene, -humulene, and germacrene D (da Trindade, da Silva, & Setzer, 2018). *Copaiba* oil has been extensively studied for its millenary healing properties, including wound healing, 175 antifungal, antileishmanial, anti-inflammatory, antioxidant, anxiolytic, immune-stimulating and antimutagenic properties. In addition, its immune-modulatory activity was also recently demonstrated where *Copaifera* oleoresins exert an activating profile in human monocytes, without affecting cell viability, and diterpene or sesquiterpene acids would be involved in their mechanisms of action (Santiago et al., 2015). In this context 180 we suggest that *Copaiba* essential oil could be beneficial to help prevent severe forms of SARS-COV-2, through its immune-stimulating, antiviral and anxiolytic properties, as a complementary therapy alternative for SARS-COV-2.

5. RED THYME ESSENTIAL OIL/THYMOL

Warm and herbaceous, Thyme is an anti-inflammatory powerhouse. Red Thyme has more antimicrobial thymol than its genetic siblings, making it well-suited for aromatherapeutic immune system support. Diffuse this essential oil during the cold and flu season to promote respiratory health and circulation. Health benefits of Red Thyme including detoxifier, improves circulation, immune system booster, and extremely strong antioxidant.

Red Thyme essential oil is composed of different volatile compounds present in the plant that are responsible for its characteristic smell. These compounds belong to the family of terpenes, among them, thymol is the majority component of thyme essential oil. Both thymol and thyme essential oil have long been used in traditional medicine as expectorant, anti-inflammatory, antiviral, antibacterial, and antiseptic agents, mainly in the treatment of the upper respiratory system (Kowalczyk et al., 2020). Several compounds found in Essential Oils, including thymol, have been studied in molecular docking, for their possible ability binding to SARS-COV-2. Molecules like thymol, camphene, pulegone, ocimene and menthol showed to present good binding affinities in this model (Kulkarni et al., 2020). Both the United States Environmental Protection Agency (EPA) in the USA and the Government of Canada have placed on the list of disinfectants with evidence for use against COVID-19 preparations with thymol as the active ingredient. These products are designed to disinfect external hard surfaces and hands in healthcare, institutional, or residential applications (Kowalczyk et al., 2020).

6. EUCALYPTUS ESSENTIAL OIL

*Eucalyptus* is extensively planted for pulp, plywood, solid wood production, but its leaf aromatic oil has astounding widespread biological activities including antimicrobial, antiseptic, antioxidant, chemotherapy agent, respiratory and gastrointestinal disorders treatment, wound healing, and insecticidal/insect repellent, herbicidal, acaricidal, nematocidal, and perfumes, soap making and grease remover. The antimicrobial activity of the *Eucalyptus* essential oil has been studied by several researchers. *Eucalyptus* essential oils and their major constituents exhibit toxicity against a wide range of microbes including bacteria, fungi, soil-borne and post-harvest pathogens. Traditional healers use *Eucalyptus* to treat many illnesses such as infections, colds, flu, sore throats, bronchitis, pneumonia, aching, stiffness, and neuralgia. The *Eucalyptus* oil's antimicrobial activity could be attributed due to the presence of compounds like 1,8-cineole, α-pinene, β-pinene and limonene (Dhakad, Pandey, & Rawat, 2018) Leaf essential oils of *E. amplifolia, E. blakelyi, E. globulus, E. grandis, E. incrassata, E. tereticornis*, also have inhibitory effect on Epstein-Barr virus activation. The result shows that euglobals have strong inhibitory activity against the viruses. Anti-viral activity against herpes simplex virus (HSV-1, HSV-2) has also been demonstrated in cell culture. Rotavirus Wastrain, Coxsackievirus B4, and herpes virus type-1 were affected by *E. camaldulensis* essential oil with percentage of reduction 50, 53.3 and 90%, respectively. A study conducted in Tunisia reveals that significant antiviral activity was shown with the essential oils of *E. bicostata* and *E. astringents*, followed by essential oils of *E. cinerea* and *E. maidennii* against the Coxsakievirus B3 (Dhakad et al., 2018). A scientific review in which several plants were studied as potential coadjuvants in the treatment of COVID-19, concluded that *Eucalyptus globulus* may be useful in the relief of symptoms associated with upper respiratory infection by exerting a soothing effect on the respiratory tract (Silveira et al., 2020).

7. PROPOLIS

The word "propolis" is derived from Greek to mean defense for "pro" and city or community for "polis", or the beehive, in other words. Propolis functions in sealing holes and cracks and for the reconstruction of the beehive. It is also used for smoothing the inner surface of the beehive, retaining the hive's internal temperature (35° C.), preventing weathering and invasion by predators. Furthermore, propolis hardens the cell wall and contributes to an aseptic internal environment. Propolis generally becomes soft and sticky upon heating. It also possesses a pleasant smell. Propolis and its extracts have numerous applications in treating various diseases due to its antiseptic, anti-inflammatory, antioxidant, antibacterial, antimycotic, antifungal, antiulcer, anticancer, and immunomodulatory properties (Pasupuleti, Sammugam, Ramesh, & Gan, 2017). Propolis extracts from temperate climate have been shown to possess a potent and broad-spectrum antiviral activity against a diverse panel of viruses such as HSV-1, HSV-2, Influenza virus type A and B, Parainfluenza virus, Adenovirus, HIV, infectious bursal disease virus and avian reovirus, Newcastle virus disease, bovine rotavirus, pseudorabies virus, feline calicivirus, canine adenovirus type 2, and bovine viral diarrhea virus.

Proposed mechanisms of antiviral activity include inhibition of virus entry into the cells, and disruption of the viral replication machinery. In addition to its effect on virus multiplication, propolis was also found to exert a virucidal action on the enveloped viruses, such as is the Coronavirus. (Bachevski, Damevska, Simeonovski, & Dimova, 2020).

Propolis components have inhibitory effects on the ACE2, TMPRSS2 and PAK1 signaling pathways; in addition, antiviral activity has been proven in vitro and in vivo. In pre-clinical studies, propolis promoted immunoregulation of pro-inflammatory cytokines, including reduction in IL-6, IL-1 beta and TNF-α. This immunoregulation involves monocytes and macrophages, as well as Jak2/STAT3, NF-kB, and inflammasome pathways, reducing the risk of cytokine storm syndrome, a major mortality factor in advanced COVID-19 disease (Berretta, Silveira, Cóndor Capcha, & De Jong, 2020). Propolis has also shown promise as an aid in the treatment of various of the comorbidities that are particularly dangerous in COVID-19 patients, including respiratory diseases, hypertension, diabetes, and cancer. Standardized propolis products with consistent bioactive properties are now available. Given the current emergency caused by the COVID-19 pandemic and limited therapeutic options, propolis is presented as a promising and relevant therapeutic option that is safe, easy to administrate orally and is readily available as a natural supplement and functional food (Berretta et al., 2020).

8. VIRGIN COCONUT OIL (ORGANIC)

Virgin coconut oil is extracted from the fresh milk of coconut using cold process which maintains all the natural constituents, aroma, and antioxidants of the oil. According to the Ayurveda—teaching inscribed in the oldest scripture of Hinduism (circa 1500 BC)—coconut oil nourishes the body and increases strength. The chemical composition of coconut oil is complex, and although it is mainly made up of medium chain fatty acids, it also presents other bioactive compounds such as phenolic compounds, phospholipids, tocopherols (vitamin E) and sterols (Deen et al. 2021). Modern research has now found a common link between these two natural health products—their lipid content. The medium chain fatty acids and monoglycerides found primarily in coconut oil have miraculous healing power which act as natural antibiotic and help modulate immunity. Coconut oil, either topically applied or ingested, gets broken down to release Lauric Acid and Monolaurin—known antimicrobial agents. The studies reported in literature are discussed to evaluate the antiviral, antibacterial and antifungal benefits of coconut oil. Not only does coconut oil metabolites have antimicrobial activity but also these remarkable derivatives have been shown not to cause resistance organisms to appear. The anti-microbial mechanistic action also helps activate the anti-inflammatory nature of the immune response in human body. In vitro, animal, and human studies support the potential of coconut oil as effective and safe immune-nutritive active (Joshi et al. 2020).

9. SUNFLOWER LECITHIN

Lecithin is essential to your body. Sunflower lecithin is rich in choline and other essential fatty acids such as phosphatidylinositol, and some people take it as a supplement. Lecithin supplements have been shown to help with acne and improve liver function. Some also use it for improving cholesterol levels, arthritis, and high blood pressure.

Lecithin comes from the Greek lekithos, meaning egg yolk, and is a term used to describe yellow-brownish fatty substances that occur naturally in plant tissues, such as sunflower. It is used in food to provide a smooth, moist texture and to keep ingredients from separating. Sunflower lecithin has positive health benefits while also holding nature ingredients together.

10. YELLOW BEE WAX

Yellow beeswax has mild anti-swelling (anti-inflammatory) effects. There is also some evidence that it might help protect the stomach. As medicine, beeswax is used for lowering cholesterol and for relieving pain. It is also used for swelling (inflammation), ulcers, diarrhea, and hiccups. In foods and beverages, yellow beeswax is used as stiffening agents.

11. EXTRA VIRGIN OLIVE OIL

This oil is obtained by cold pressing of olives. It contains monounsaturated fatty acids, and several polyphenols including oleuropein and hydroxytyrosol, which have several antioxidative and anti-inflammatory properties, which can be linked with significant antiviral and antibacterial potential. Oleuropein has shown a potential antiviral activity against respiratory syncytial virus (RSV), a common upper respiratory infection virus. This effect has been attributed to the antioxidative property of elenolic acid as a main fragment in oleuropein, which has long been shown to have potent antiviral activities against herpes, influenza A and B, and parainfluenza 1, 2, and 3 viruses. The antioxidation protective benefits of Olive oil, especially Extra-Virgin Olive Oil, which has a higher phenolic content, promotes its role for enhancing the immune system defense against viruses (Alkhatib 2020).

12. ANTIVIRAL PROPERTIES OF ESSENTIAL OILS

Essential oils (EOs) have long been known to have anti-inflammatory, immunomodulatory, broncho dilators, and antiviral properties and are being proposed to have activity against SARC CoV-2 virus. Owing to their lipophilic nature, EOs are advocated to penetrate viral membranes, easily leading to membrane disruption. Moreover, EOs contain multiple active phytochemicals that can act synergistically on multiple stages of viral replication and induce positive effects on host respiratory system 320 including bronchodilation and mucus lysis (Asif, Saleem, Saadullah, Yaseen, & Al Zarzour, 2020).

The mechanisms of action of essential oils (EOs) are versatile due to the complexity of composition and synergism of bioactive compounds compared to synthetic antiviral substances (e.g., acyclovir) that act in a manner specific to a particular type of virus. The action of EOs can interfere with the extracellular level, i.e., the penetration of the virus into the host cell, interfering with the structure of the viral envelope, or block viral proteins that are necessary for the virus to enter the host cells. EOs can also have antiviral effects against intracellular viruses. The mechanisms are not yet fully understood. (Kowalczyk, Przychodna, Sopata, Bodalska, & Fecka, 2020).

13. DISCLAIMER

The said soft gel is produced and sold as a food supplement in compliance with relevant American food supplement regulations. Therefore, and in accordance with all regulations regarding such, the information contained herein, does not make any specific claims concerning the efficacy of the disclosure soft gel as a COVID cure.

14. BIBLIOGRAPHY

1. Alkhatib, Ahmad. 2020. "Antiviral Functional Foods and Exercise Lifestyle Prevention of Coronavirus." Nutrients 12 (9): 1-17.
2. Asif, M., Saleem, M., Saadullah, M., Yaseen, H. S., & Al Zarzour, R. (2020). COVID-19 and therapy with essential oils having antiviral, anti-inflammatory, and immunomodulatory properties. Inflammopharmacology, 28(5), 1153-1161.
3. Bachevski, D., Damevska, K., Simeonovski, V., & Dimova, M. (2020). Back to the basics: Propolis and COVID-19. Dermatologic Therapy, 33(4).
4. Berretta, A. A., Silveira, M. A. D., Cóndor Capcha, J. M., & De Jong, D. (2020). Propolis and its potential against SARS-COV-2 infection mechanisms and COVID-19 disease. Biomedicine & Pharmacotherapy, 131(January), 110622.
5. Brink, L. R., Chichlowski, M., Pastor, N., Narayanappa, A. T., & Shah, N. (2021). In the age of viral pandemic, can ingredients inspired by human milk and infant nutrition be repurposed to support the immune system? Nutrients, 13(3), 1-28.
6. da Trindade, R., da Silva, J. K., & Setzer, W. N. (2018). *Copaifera* of the neotropics: A review of the phytochemistry and pharmacology. International Journal of Molecular Sciences, 19(5).
7. Dhakad, A. K., Pandey, V. V, & Rawat, J. M. (2018). Biological, medicinal and toxicological significance of J Sci Food Agri, 98(3), 833-848.
8. Dofferhoff, A. S. M., Piscaer, I., Schurgers, L. J., Visser, M. P. J., van den Ouweland, J. M. W., de Jong, P. A., . . . Janssen, R. (2020). Reduced Vitamin K Status as a
9. Potentially Modifiable Risk Factor of Severe Coronavirus Disease 2019. Clinical Infectious Diseases, (Xx), 1-8.
10. Kowalczyk, A., Przychodna, M., Sopata, S., Bodalska, A., & Fecka, I. (2020). Thymol and Thyme Essential Oil—New Insights into Selected Therapeutic Applications. Molecules, 25(18), 4125.
11. Kulkarni, S. A., Nagarajan, S. K., Ramesh, V., Palaniyandi, V., Selvam, S. P., & Madhavan, T. (2020). Computational evaluation of major components from plant essential oils as potent inhibitors of SARS-COV-2 spike protein. Journal of Molecular Structure, 1221, 128823.
12. Lieberman, S., Enig, M. G., & Preuss, H. G. (2006). A Review of monolaurin and lauric acid.
13. Alternative & Complementary Therapies, 12(6), 310-314.
14. Pasupuleti, V. R., Sammugam, L., Ramesh, N., & Gan, S. H. (2017). Honey, Propolis, and Royal Jelly: A Comprehensive Review of Their Biological Actions and Health Benefits. Oxidative Medicine and Cellular Longevity.
15. Pereira, M., Dantas Damascena, A., Galvão Azevedo, L. M., de Almeida Oliveira, T., & da Mota Santana, J. (2020). Vitamin D deficiency aggravates COVID-19: systematic review and meta-analysis. Critical Reviews in Food Science and Nutrition, 0(0), 1-9.
16. Santiago, K. B., Conti, B. J., Murbach Teles Andrade, B. F., Mangabeira da Silva, J. J., Rogez, H. L. G., Crevelin, E. J., . . . Sforcin, J. M. (2015). Immunomodulatory action of *Copaifera* spp oleoresins on cytokine production by human monocytes. Biomedicine and Pharmacotherapy, 70(C), 12-18.
17. Silveira, D., Prieto-Garcia, J. M., Boylan, F., Estrada, O., Fonseca-Bazzo, Y. M., Jamal, C. M., . . . Heinrich, M. (2020). COVID-19: Is There Evidence for the Use of Herbal Medicines as Adjuvant Symptomatic Therapy? Frontiers in Pharmacology, 11(September), 1-44.
18. Vlasschaert, C., Goss, C. J., Pilkey, N. G., Mckeown, S., & Holden, R. M. (2020). Vitamin k supplementation for the prevention of cardiovascular disease: Where is the evidence? a systematic review of controlled trials. Nutrients, 12(10), 1-25.

19. Yisak, H., Ewunetei, A., Kefale, B., Mamuye, M., Teshome, F., Ambaw, B., & Yitbarek, G. Y. (2021). Effects of vitamin d on covid-19 infection and prognosis: A systematic review. Risk Management and Healthcare Policy, 14, 31, 38.

The invention claimed is:

1. A composition for use as a dietary supplement comprising approximately 700 mg extra virgin olive oil (cold-press), approximately 500 mg monolaurin, approximately 50 mcg vitamin D3, approximately 120 mcg vitamin K2, approximately 50 mg *Copaiba* balsam oil, approximately 50 mg *Eucalyptus* Oil, approximately 25 mg Red Thyme Oil, approximately 50 mg Virgin Coconut Oil, approximately 50 mg Propolis Powder Extract, approximately 100 mg Yellow Beeswax, and approximately 15 mg Sunflower Lecithin; wherein the composition is formulated in to two soft gels capsules, wherein the composition is used to nourish and boost the immune system.

2. A method for nourishing and boosting the immune system; comprising: administering the composition of claim 1 wherein one soft gel is orally administered in the morning and one soft gel is orally administered in the afternoon, wherein the composition is consumed by mouth after a meal.

* * * * *